United States Patent [19]

Moll

[11] Patent Number: 5,270,175

[45] Date of Patent: Dec. 14, 1993

[54] METHODS AND COMPOSITIONS FOR PRODUCING METABOLIC PRODUCTS FOR ALGAE

[75] Inventor: Benjamin A. Moll, Berkeley, Calif.

[73] Assignee: DNA Plant Technology Corporation, Oakland, Calif.

[21] Appl. No.: 729,513

[22] Filed: Jul. 12, 1991

[51] Int. Cl.⁵ .................. C12N 5/14; C12N 15/82; A01H 13/00; C12P 7/06
[52] U.S. Cl. .................. 435/41; 435/69.1; 435/70.1; 435/161; 435/172.3; 435/320.1; 435/946; 435/240.2; 536/23.2; 935/14; 935/23; 935/35; 935/67; 800/205; 800/200; 800/DIG. 7
[58] Field of Search .............. 435/69.1, 70.1, 161, 435/172.3, 240.4, 320.1, 946; 935/23, 35, 67; 800/200, 205, DIG. 7

[56] References Cited

U.S. PATENT DOCUMENTS

| | | | |
|---|---|---|---|
| 4,962,028 | 10/1990 | Bedbrook et al. | 435/172.3 |
| 5,028,539 | 7/1991 | Ingram et al. | 435/161 |
| 5,084,385 | 1/1992 | Ashikari et al. | 435/96 |

FOREIGN PATENT DOCUMENTS

| | | |
|---|---|---|
| 0108580 | 5/1984 | European Pat. Off. |
| WO92/16615 | 10/1992 | PCT Int'l Appl. |

OTHER PUBLICATIONS

Bennetzen et al. "The Primary Structure of the Saccharomyces..." J. Biol. Chem 257:3018–3025 (Mar. 1982).
Kellermann, E. et al. "Analysis of the Primary Structure and ..." Nuac Acids Res. 14:8963–8977 (Nov. 1986).
Stokes, H. W. et al. "Recombinant genetic approaches for efficient . . . " Energy Research Abstracts 11(6) Abstract 11145 (Mar. 1986).
Bold, H. C. et al. (eds) "Introduction to the Algae" Prentice-Hall Inc. Englewood Cliffs. N.J. pp. 191–204 (1985).

*Primary Examiner*—Robert A. Wax
*Assistant Examiner*—Rebecca Prouty
*Attorney, Agent, or Firm*—Townsend and Townsend Khourie and Crew

[57] ABSTRACT

Soluble metabolic products, such as ethanol, are produced by growing modified algal cells in a growth medium and recovering the products from the growth medium. The algal cells are modified to overproduce the metabolic product by providing for overexpression of at least one enzyme in the metabolic pathway for the product. For the production of ethanol, the alcohol dehydrogenase gene, the pyruvate decarboxylase gene, or both, are overexpressed, typically under the control of a heterologous promoter. The algal cells may be modified by transformation with a DNA construct including coding sequence(s) of the enzyme(s) under the control of a heterologous promoter.

16 Claims, No Drawings

METHODS AND COMPOSITIONS FOR PRODUCING METABOLIC PRODUCTS FOR ALGAE

BACKGROUND OF THE INVENTION

The present invention relates generally to the transformation and use of algal cells for the production of metabolic products and, in particular, to the use of transformed algal cells for producing ethanol.

Current approaches to use and management of energy resources have several associated problems, such as pollution and $CO_2$ generation, but cost remains a key consideration. Oil and coal continue to be less expensive, at least in the short term, than alternative sources. Attempts have been made to utilize other energy sources, but competitive methods remain marginal. An attractive approach is to use solar power, since the input energy is free and inexhaustible. The cost of energy harvesting solar power, however, is prohibitively high with present technology so that it is used primarily in remote areas where less expensive energy sources are unavailable.

Plants utilize light energy, and they are by far the least expensive means of converting light energy to chemical form. The problem with using plants as an energy source derives from the costs and inefficiencies associated with harvesting, processing and conversion to usable form. If these problems can be overcome, then energy farming will be economical.

Techniques for obtaining energy from plant sources include fermentation of crops to ethanol (Winston (1981), Ethanol fuels, Solar Energy Research Institute) including corn, other grains, potatoes, sugar cane and sugar beets, and fermentation to methane (Wise (1981) Fuel Gas Production from Biomass, CRC Press, Boca Raton) or ethanol (Lynd et al. (1991) Science 251:1318-1323) of biomass, including wood, crop residues, and algae.

One of the more successful of these approaches is sugar cane fermentation. In the U.S., corn is an economical starting material (Winston (1981) supra). Biomass fermentation is economical when starting materials are waste with a very low or negative value, but it is not a competitive use of farmland. Biomass fermentation to ethanol is expected to become more economical as a result of technical advances, and it may contribute substantially to our energy budget in the future (Lynd et al. (1991) supra).

Algal systems for use in fermentation suffer from two disadvantages: the low value of the final product and high production costs. Microalgae require constant stirring to prevent adhesion to pond bottoms and must be harvested by filtration of very large volumes of water. Macroalgae methods have excessive capital costs, principally for harvesting equipment, Bird, K. T., Benson, P. H., eds., 1987. Seaweed cultivation for renewable resources, Elsevier, Amsterdam.

SUMMARY OF THE INVENTION

Soluble metabolic products are produced by growing algal cells in a growth medium and recovering the products which have been secreted into the medium. The algal cells have been modified to produce or overproduce metabolic products by overexpression of at least one enzyme in a metabolic pathway for the product. Usually, the metabolic pathway will be a pathway which is naturally present in the algal cells which has been modified, and the modification will provide for a constitutive or inducible expression of an enzyme at levels which provide for enhanced production of the metabolic product in comparison with wild-type (unmodified) algal cells. Such overexpression is typically achieved by placing a gene encoding the enzyme under the control of a heterologous promoter which provides for overexpression of the enzyme. Alternatively, overexpression may be achieved by introducing multiple copies of the enzyme gene into the algal cells.

In the exemplary embodiment, the metabolic product is ethanol and the enzyme is alcohol dehydrogenase (ADH) or pyruvate decarboxylase (PDC), preferably both. The algal cells are modified to express genes encoding for ADH and/or PDC under the control of a heterologous high expression level promoter, such as the promoter of the algal ribulose bisphosphate carboxylase small subunit gene (SSU) or the algal pyruvate kinase gene.

The present invention also comprises DNA constructs suitable for transforming algal cells to produce or overproduce a metabolic product. The DNA constructs include a DNA sequence encoding an enzyme in the metabolic pathway and a heterologous promoter sequence connected to the 5'-end of the DNA sequence. The promoter will be capable of providing for overexpression of the enzyme under at least some algal growth conditions. In the exemplary case of ethanol production, the DNA sequence will encode the PDC or ADH gene, preferably both, and the heterologous promoter sequence will encode the SSU promoter or the pyruvate kinase promoter.

The present invention still further provides for algal cells which are capable of overexpressing at least one enzyme in a metabolic pathway for a soluble metabolic product. In the exemplary case of alcohol production, the algal cells will be capable of overexpressing PDC, ADH, or preferably both. Such algal cells may be obtained by transforming wild-type or preselected algal cells with the DNA constructs described above.

The use of algae for producing soluble metabolic products will have many advantages. The algae need never be harvested from growth ponds, nor do they need to be stirred, thereby greatly reducing pond costs. The algae are desirably of a species that can form long-lived dense stands. Purification of product from the water phase is preferably accomplished by distillation or membrane separation.

In a preferred form, algal systems tolerant of saline conditions are used so that seawater or brackish water can be used in irrigation of areas, e.g., desert areas, with very low cost land. Overall, algal systems also have a potential for very high productivity, since they have no stems or roots requiring metabolic support.

DESCRIPTION OF THE SPECIFIC EMBODIMENTS

According to the present invention, algal cells will be modified to produce or overproduce a metabolic product, particularly ethanol. Overproduction of the metabolic product is defined relative to production of the product in the wild-type algal cells prior to modification. That is, the modified cells will produce greater amounts of the metabolic product under at least some algal growth conditions in comparison to the same strain of algal cells prior to modification. Usually, the modified algal strains will be able to produce at least about 100% (weight percent) greater amounts of the metabolic product, more usually producing at least about 500% greater amounts, and preferably producing at least about 1000% greater amounts.

In particular, the algal cells of the present invention will be modified to overexpress at least one enzyme in a metabolic pathway for the metabolic product. Overexpression of the enzyme is also defined relative to the enzyme expression and the unmodified algae. In particular, overexpression of the enzyme means that greater amounts of the enzyme will be produced under at least some growth conditions than are produced by the unmodified algal cells.

Overexpression of the enzyme may be achieved either by introducing multiple copies of the gene under the control of a naturally-associated promoter or heterologous promoter or by introduction of a single copy of the enzyme under the control of a heterologous promoter capable of providing the desired overexpression. By heterologous promoter, it is meant that the promoter is one not naturally associated with the enzyme gene in an algal host. The promoter may be associated with other algal genes or may be obtained from non-algal sources, including bacteria, viruses, yeast, plant, and mammalian cells, and the like. The promoter may be constitutive or inducible.

A. SELECTION AND ISOLATION OF AN ORGANISM SUITABLE FOR MODIFICATION ACCORDING TO THE PRESENT INVENTION

1. Taxonomic and Functional Characteristics of Suitable Organisms

The desired algal organism should be photosynthetic, tolerant of field conditions (including available water supplies) in the specified geographical region, without substantial barriers to diffusion of small molecules between the cells of the plant and the surrounding medium. The algae should be tolerant of prolonged submersion. The algae should grow attached to the pond bottom or grow in a mat that is not readily dislodged by gently flowing water.

Algae suitable for use with the invention are non-unicellular algae which form thallic structures (e.g., filaments, blades, leaf-like structures, or more comlex structures such as stipes, holdfasts and fronds). Such structures permit the algae to attach to the pond bottom and to form mats. They also allow formation of large quantities of biomass.

Suitable algae may be chosen from the following divisions of algae: green algae (Chlorophyta), red algae (Rhodophyta), brown algae (Phaeophyta) or blue-gree algae (Cyanophyta). Suitable orders of green algae are Ulvales, Ulotrichales, Schizogoniales, Oedogoniales, Zygnematales, Cladophorales, Siphonales, and Dasycladales; Smith (1955), supra. Preferred orders are Cladophorales and, in particular, Ulvales. Cladophorales has members that grow in appropriate habitats in both freshwater and marine environments. Ulvales is especially suited for marine applications and is well adapted for full sunlight and large changes in salinity. Within the order of Ulvales preferred genera are the genus Enteromorpha, e.g., species *E. linza, E. intestinalis* and *E. micrococcus;* the genus Ulva, e.g., *U. taeniata;* and the genus Monostroma, e.g., *M. zostericola.* Enteromorpha is a particularly preferred genus. See Smith, G. M. (1969) Marine algae of the Monterey Peninsula, Stanford University Press, Stanford. Chlorophyta orders Volvocales (e.g., Chlamydomonas), Chlorococcales and Tetrasporales do not form multicellular thalli.

Suitable genera of Rhodophyta are Porphyra, Chondrus, Gelidium and Agardhiella. Suitable genera of Phaeophyta are Laminaria, Undaria, Macrocystis, Sargassum and Dictyosiphon. A suitable genus of Cyanophyta is Phoridium. See Cheney (1986), In: *Algal Biomass Technologies,* Barclay et al. (eds.), J. Cramer, Berlin; and Smith (1955), supra.

2. Isolation of Candidate Alga

The first step in the determination of a suitable organism is isolation from nature. The organism preferably will tend to dominate the growth habitat that will be provided for it. This will minimize subsequent problems with weed control. During establishment phase, fertilizer is used to bring about rapid growth. Effects of mineral supplements on algal growth are well known (Lewin (1962) (ed.) *Physiology and Biochemistry of the Algae,* Academic Press, New York).

3. Verification of Suitability

The organism to be used should satisfy certain design criteria. It should have adaquate photosynthetic rate, preferably resulting in over 15 g/m$^2$-day carbohydrate accumulation, more preferably over 30 g/m$^2$-day and most preferably over 60 g/m$^2$-day. These values are determined using established methods for measurement of photosynthetic rate such as gas-exchange (Jassby, (1978), Polarographic measurements of respiration following light-dark transitions. In: *Handbook of Phycological Methods,* Hellebust et al. (eds.) Cambridge University Press, Cambridge, pp. 298–303), using, for example, oxygen electrode or infra-red $CO_2$ detector, or by measuring starch accumulation, using, for example, $H_2SO_4$-phenol measurement of reducing sugar content (Kochert (1978), Carbohydrate determination by the phenol-sulfuric acid method. In: *Handbook of Phycological Methods,* Hellebust et al. (eds.), Cambridge University Press, Cambridge, pp. 96–97).

Tolerance for varying salt concentration is required for seawater or brackish water applications. The organism should tolerate at least a 10% increase in salt concentration, preferably a 50% increase in salt concentration, and most preferably a two fold or higher increase in salt concentration. The organism preferably will tolerate some period of exposure to the air, preferably several hours. Tolerance to salt conditions is determined by observing growth rate or gas exchange or starch accumulation under different conditions of salt concentration. Tolerance to drying is determined by observing survival of algae subjected to various periods of drying.

The alga preferably should have capacity to store starch reserves representing at least one day of photosynthesis, preferably several days and most preferably more than 10 days of photosynthesis. Starch storage capacity is measured by determining starch content of unfermented algae, using, for example, the $H_2SO_4$-phenol reducing sugar measurement.

The algal mat preferably should have acceptable rates of night respiration, less than the net daily photosynthesis, preferably less than ½ of the net photosynthesis, and most preferably less than 1/10 of the net daily photosynthesis. Respiration is determined using the same methods as are appropriate for photosynthesis measurements (Jassby, (1978) supra).

Capacity for fermentation should exist so that genetic engineering can tie into existing metabolic pathways. Maximum glycolytic activity preferably should be at least 1.5 times the night respiration rate, more preferably over 5 times the night respiratory rate, and most preferably over 10 times the night respiratory rate. Capacity for fermentation is determined by measuring respiration under conditions that stimulate it to a maximal degree. The rate found is the rate of the slowest step in the respiratory pathway (Savageau, (1976), Biochemical systems analysis, Addison-Wesley Publishing Company, London). Capacity for fermentation depends on the potential rate of glycolysis (Goodwin et al. (1983), Introduction to plant biochemistry, Pergamon Press, Oxford), but not on the other steps in the respiratory path, so this measurement is a lower bound on the capacity for fermentation. Measurement techniques that are appropriate for respiratory rate determinations are useful for this measurment as well. Conditions that stimulate respiration may be, for example, the use of uncouplers, for example, dinitrophenol (Goodwin et al. (1983) supra).

The alcohol concentration that is achieved in a single pass of fermentation depends on the growth density of the algae (grams fresh weight per cc) and the fermentable starch content (mg per gram). The growth density of the algae is determined by taking a sample of algal mat with known dimensions, removing any adherent non-algal material, removing water by, for example, centrifugation or blotting, and weighing. Growth density is calculated as the weight divided by the sample volume. The starch content of a sample with known fresh weight, determined as described above, is used to determine the starch content per unit volume. This is the product of the growth density times the starch per unit weight. The maximum potential alcohol concentration that can be achieved is equal to the starch per unit volume times about 0.51 (weight ethanol produced/weight carbohydrate consumed). The increase in alcohol concentration from a single pass of fermentation is preferably over 0.1%, more preferably over 1%, and most preferably over 5%. The fermentation medium is used on several cultures until the alcohol concentration has reached the desired level, determined by economic considerations and the tolerance of the organism to alcohol.

Preferably, the organism tolerates alcohol concentrations of at least about 1%, preferably higher, e.g., about 6%. This is determined by observing survival of algae in seawater containing various levels of alcohol.

Algal morphology that prevents drainage is undesirable. Drainage time for a 100 m square field is preferably less than 24 hours, most preferably less than twelve hours. The measurement and prediction of drainage times is well known to those skilled in the art.

B. SELECTION OF A SUITABLE BIOCHEMISTRY

1. Characteristics of a Suitable Fermentation

The product of fermentation should be a compound to which the cell membrane is permeable, or for which a carrier system exists or can be created. It should be possible to separate the product from the growth medium. Preferably, it is possible to stimulate the production or excretion of the product.

2. Biochemistry of Ethanol Production

A preferred fermentation is production of ethanol. Ethanol is produced by many different organisms. It is produced as follows: pyruvate is decarboxylated to form acetaldehyde and acetaldehyde is reduced to form ethanol (Goodwin et al. (1983) supra). These steps are mediated by two enzymes, pyruvate decarboxylase (PDC) and alcohol dehydrogenase (ADH). For present purposes, PDC is any enzyme which in a single step mediates decarboxylation of pyruvate to yield acetaldehyde. ADH is any enzyme which in a single step mediates reduction of acetaldehyde to ethanol. All the other enzymes required for these purposes are part of the glycolysis system, and they are found in essentially all organisms (Gibbs (1962) Respiration. In: *Physiology and Biochemistry of the Algae,* Lewin (ed.) Academic Press, New York. (Ethanol can also be produced in an acetate/formate/ethanol producing pathway known in both bacteria and algae (Kreuzberg (1984) Physiol. Plant. 61:87–94; Kreuzberg (1985) Planta 163:60–67; and Knappe et al. (1975) Methods Enzymol. 41:508–518). The pyruvate-acetaldehyde-ethanol pathway is widely distributed in nature. It occurs in bacteria (Swinfs et al. (1977) Bacteriol. Rev. 41:1–46), yeast (Fraenkel (1982) In: *The Molecular Biology of the Yeast Saccharomyces,* Strathern et al. (eds.), Cold Spring Harbor Laboratory, Cold Spring Harbor), algae (Kreuzberg et al. (1987) Physiol. Plantarum 69:481–488; Gibbs (1962) In: *Physiology and Biochemistry of the Algae,* Lewin (ed.) Academic Press, New York), and higher plants (Goodwin et al. (1983) supra).

Under anaerobic conditions, ATP is generated by glycolysis, resulting in the production of reduced NADH and pyruvate (Goodwin et al. (1983) supra). (Under aerobic conditions, pyruvate is utilized in the TCA cycle and NADH is utilized by the electron transport system to produce ATP.) The utilization of NADH and pyruvate is quite variable, and numerous pathways exist (Davies (1980) In: *The Biochemistry of Plants,* Academic Press, New York, Vol. 2, pp. 581-611). Production of ethanol is one possible pathway. An example of another pathway is production of lactic acid. Regulation of glycolysis is such that if fermentation pathway enzymes are all abundant, the rate of fermentation is determined by ATP demands (Fraenkel (1982). supra).

Certain algae that have been studied in regard to fermentation are not desirable for this method of alcohol production. In Chlamydomonas and certain other green algae in which fermentation has been studied, the products of fermentation may include formic acid, acetate, lactate, hydrogen, glycerol, $CO_2$ and ethanol (Kreuzberg (1984), supra; Kreuzberg (1985), supra; Knappe et al. (1975) supra; Kreuzberg (1987) supra; and Klein et al. (1978) Plant Physiol. 61:953-956). The principal products of fermentation depend on conditions and species. Fermentation products may change with time: in Chlamydomonas, fermentation is at first almost exclusively the formate/acetate/ethanol type, later with substantial amounts of ethanol/$CO_2$ with some hydrogen, glycerol and lactic acid. Coincident with the shift in fermentation products there is a decline in the rate of substrate utilization. Lower pH reduces the activity of the primary fermentation pathway in Chlamydomonas, and secondary pathways become more important, but other controls may exist. This is reminiscent of the situation in higher plants in which fermentation at first produces lactic acid, and later mainly ethanol. The shift in fermentation products in higher plants is believed to be a consequence of acidification. Gene induction during anaerobiosis is well characterized in higher plants, and includes genes coding for fermentation enzymes (Sachs et al. (1980) Cell 20:761-767; and Laszlo et al. (1983) Mol. Gen. Genet. 192:110-117).

3. Engineering Ethanol Production

Ethanol production in algae can be engineered by expressing PDC and ADH in the host cells, using DNA constructs and transformation methods as described below. Other suitable constructs which may be used in the present invention are described in U.S. Pat. No. 5,000,000, the disclosure of which is incorporated herein by reference. The fraction of pyruvate that is processed to alcohol depends on the relative rates of alcohol production and competitive endogenous fermentation reactions. PDC and ADH activities are preferably high enough that competitive anaerobic pathways account for less than 50% of carbon flow, and most preferably less than 10%. PDC activity should be low enough during aerobic periods that total carbohydrate utilization in the dark is less than the net daily photosynthesis, preferably less than ½ and most preferably less than 1/10 of the net daily photosynthesis. Expression sufficient to give PDC and ADH levels of 0.001% of total protein is sufficient (assuming specific activity of 500 U/mg, dry weight equal to 0.169×fresh weight, protein 10% of dry weight, U equals 1 micromole alcohol/min) to give a fermentation rate of about 90 micromoles per gram dry weight per hour, or over 100 grams carbohydrate per $m^2$-day for a 10 kg/$m^2$ mat.

Transformants engineered with PDC alone are screened for PDC activity. This screening is done in both aerobic and anaerobic conditions. Under anaerobic conditions, PDC activity will result in conversion of pyruvate to acetaldehyde. Under aerobic conditions, pyruvate pool size and PDC activity are preferably small enough that pyruvate is utilized mainly by aerobic respiration. If PDC is under the control of an anaerobicly induced promoter, this will be reflected in a screen that allows a sufficient period of time for the response to anaerobiosis. The time permitted for anaerobic induction is preferably several hours, e.g., 12 hours. Screening under both aerobic and anaerobic conditions permits selection of transformants with high levels of PDC and good regulation of PDC activity. PDC can be assayed by well known methods (Neale et al. (1987) J. Bacteriol. 169:1024-1028), e.g., in a reaction mix which includes pyruvate, NADH and ADH, pyruvate decarboxylase activity results in production of acetaldehyde, which, in a reaction catalyzed by ADH, produces alcohol and results in oxidation of NADH, which is readily measured spectrophotometrically. Alternatively, reactions can be coupled to the production of colored form of pigments, to screen for enzyme activity in culture plates. For example, culture media that includes pararosaniline reacted with sodium bisulfite to produce the leuco form of the dye (Schiff reagent), will react with aldehydes to form an intense red pigment. This can be used as a non-toxic screen for aldehyde production (Conway et al. (1987) J. Bacteriol. 169:949-954).

Transformants engineered with ADH alone are screened for ADH activity. If ADH is under the control of an anaerobic promoter, the screen is preferably preceded by a period of anaerobiosis sufficient to allow development of induced protein activity. The time allowed for anaerobic induction is preferably several hours, e.g., 12 hours. ADH can be measured (Conway et al. (1987) supra) using a reaction mix which includes alcohol and NAD+. This reaction produces acetaldehyde and results in reduction of NAD+ to NADH, which is readily measured spectrophotometrically. Alternatively, reactions can be coupled to the production of colored form of pigments, to screen for enzyme activity in culture plates. This is done, for example, by including Schiff reagent and alcohol in culture media (Conway et al. (1987) supra). ADH activity results in conversion of alcohol to acetaldehyde, which reacts with Schiff reagent to produce an intensely red color. Alternatively, plants are incubated on filter paper soaked with a reaction mixture including ethanol, NAD+, Nitro Blue Tetrazolium, and phenazine methosulfate. Acetaldehyde will result in the formation of a dark precipitate (Santangelo et al. (1988) Mol. Cell. Biol. 8:4217-4224). Alternatively, plants can be selected for high ADH levels by growing under dark or dim light conditions and feeding alcohol as a major or sole energy source (Danforth (1962) In: *Physiology and Biochemistry of the Algae*, Lewin (ed.) Academic Press, New York). Under aerobic conditions, alcohol is converted to acetaldehyde by ADH, with the reduction of NAD+. Acetaldehyde is converted to acetate by aldehyde dehydrogenase, if present, with the reduction of NAD+.

Lines that are high in PDC are used as hosts for transformation with ADH, or they are combined with lines high in ADH by sexual crossing or by protoplast fusion, to produce lines that have both ADH and PDC activities. Alternatively, lines that are high in ADH are used as hosts for transformation with PDC, or they are combined as described above.

Transformants engineered with both PDC and ADH, sequentially or simultaneously, are screened for alcohol production under both aerobic and anaerobic conditions. This is done by sampling media in which the plants are subjected to the desired condition for a period of time, preferably several hours, e.g., 24 hours, and testing for alcohol. Alcohol can be detected by well known methods, e.g., in a reaction mix including NAD+ and ADH, in which alcohol is converted to acetaldehyde, resulting in reduction of NAD+, which is readily detected spectrophotometrically. Alternatively, reactions can be coupled to the production of colored form of pigments, to screen for enzyme activity in vivo. For example, filter paper soaked with a reaction mix that includes ADH, NAD+ and Schiff reagent, will convert alcohol to acetaldehyde, after which the Schiff reagent reacts with the aldehyde to form an intense red pigment. Alternatively, alcohol can be detected in vivo by, for example, incubating plants on filter paper soaked with a reaction mixture including Nitro Blue Tetrazolium, phenazine methosulfate, NAD+ and ADH. Alcohol will result in the formation of a dark precipitate.

Untransformed plants are engineered by selecting mutants or other variants that have increased levels of PDC, ADH, or some combination thereof. These screens are carried out as described above for transformed plants, and the untransformed plants are used in exactly the same way as transformed plants, serving as hosts for further engineering or as parents in crosses or donors in fusions.

C. DEVELOPMENT OF DNA CONSTRUCTS

1. Acceptable Construct Performance

The expression system utilized preferably should be active in all cell types within the host algae. Activity preferably persists in anaerobic conditions, and most preferably is higher under anaerobic conditions. The desirability of increased expression under anaerobic conditions is most pronounced for activity of the gene encoding PDC, since PDC regulates the activity of the alcohol producing pathway. The expression levels must be sufficient to give enzyme levels high enough for a fermentation at a practical rate. For a specific activity of 500 U/mg, this should be at least 0.0001% of total protein, preferably over 0.001%, and most preferably selected for optimal ethanol production. (A good higher plant expression system can give constituitive expression of 0.2% of total protein, over 1000 times the minimal requirements of this system.)

In addition, the construction used preferably has a selectable marker, a screenable marker or both, and at least one of these markers is preferably expressed in aerobic conditions. Expression of markers during anaerobiosis is acceptable but not necessary. Examples of non-selectable transformation markers are GUS (Jefferson (1987) Plant Mol. Biol. Reporter 5:387–405) and LUC (Ow et al. (1986) Science 234:856–859). Examples of selectable markers are NPTII, conferring kanamycin resistance, Van Den Elzen, P. J. M., et al. (1985), Plant Mol. Biol. 5:149–154; HPT, conferring hygromycin resistance, Van Den Elzen, P. J. M., et al. (1985), Plant Mol. Biol. 5:299–302; DHFR Mtx$^r$, conferring methotrexate resistance, Herrera-Estrella et al., (1983), EMBO J. 2:287–295; and SPT, conferring streptomycin resistance, Maliga, P. et al. (1988), Mol. Gen. Genet. 210:86–89. ADH or PDC may be used as a screenable marker, in addition to its engineering function. Marker genes are included to facilitate the isolation of transformants. They are desirable if the frequency of transformation is low enough that it is not convenient to screen plants for the gene of interest by, for example southern blot analysis, or PCR analysis. Selectable markers are desirable especially if the frequency of transformation is low enough that it is not convenient to screen for transformants.

2. Sources of PDC and ADH Coding Regions

ADH has been cloned from, and can be obtained from, several sources, including bacteria (Conway, (1987) supra), higher plants (Bennetzen et al. (1984) PNAS USA 81:4125–4128) and yeast (Bennetzen et al. (1982) J. Biol. Chem. 257:3018–3025). There is some variation in the specificity and enzyme characteristics of ADH. The yeast enzyme has a pH optimum of about 7, (Plapp et al. (1987) In: *Enzymology and Molecular Biology of Carbonyl Metabolism*, A. R. Liss, pp. 227–236). ADH can be obtained from any plant, yeast or bacterial source. Animal sources of ADH can also be used but are less desirable, since allosteric characteristics may be suited to the metabolism rather than the production of alcohol.

PDC has been cloned from, and can be obtained from, both yeast (Kellerman et al. (1986) Nucl. Acids Res. 14:8963–8977) and bacteria (Neale et al. (1987) J. Bacteriol. 169:1024–1028). The substrate affinity and allosteric properties of PDC from these two sources are different. PDC from Zymomonas mobilis shows Michaelis-Menten kinetics with a Km of about 0.3 mM. PDC from yeast has a Hill coefficient of about 2 with $K/\frac{1}{2}$ of about 1 mM. Yeast PDC is a preferred source and is amenable to being overexpressed (because of the higher $K_m$ and allosteric kinetics).

Coding sequences for PDC and ADH are obtained by standard techniques, for example, PCR amplification of cDNA (Innis et al. (1990), PCR protocols. Academic Press, New York). Another possible method is to screen a cDNA library (e.g., a library in *E. coli* (Sambrook et al. (1989) Molecular cloning. Cold Spring Harbor Laboratory Press, Cold Spring Harbor) with probes developed using the known sequences of PDC and ADH.

The coding sequence for yeast PDC is given in Kellerman et al. (1986) supra. The coding sequence for yeast ADH is given in Bennetzen (1982) supra.

3. Sources of Promoter Sequences

Promoter sequences are preferably isolated from the potential host organism or a closely related organism. Promoters that are functional in higher plants are less preferred except for groups of algae closely related to higher plants. For example, the 35S CaMV promoter, which is active in many plant species, is completely inactive in Chlamydomonas (Day et al. (1990) Physiol. Plantarum 78:254–260). Promoters that are functional in one group of algae may not be functional in another. Promoters may be tested in this regard as described below. Comparison of 5S-RNA sequences from higher plants and algae (Luersen et al. (1981) PNAS USA 78:2150–2154; Qi et al. (1988) J. Mol. Evol. 27:336–340; Darlix et al. (1981) Nucl. Acids. Res. 9:1291–1299; Lin et al. (1983) Nucl. Acids. Res. 11:1909–1912; Kumazaki et al. (1982) J. Mol. Evol. 18:293–296; Payne et al. (1976) Eur. J. Biochem. 71:33–38; Green et al. (1982) Nucl. Acids Res. 10:6389–6392; and Delihas et al. (1981) J. Biol. Chem. 256:7515–7517) shows that sequence divergence is much less within the higher plants than it is between different groups of algae.

Genes that are known to exhibit high level expression (e.g., ribulose bisphosphate carboxylase small subunit gene (SSU)) or expression under anaerobic conditions (e.g. pyruvate kinase gene) in other systems can be chosen (as promoter sources) for isolation from the host or closely related organism. Probes or primers to isolate genes are made using sequence information available from published sequences. Alternatively, cDNA libraries derived from the host or closely related organism can be screened for clones that are well expressed under aerobic and anaerobic conditions. These clones can then be used to make probes or primers. Genes can be isolated by PCR, using amplification primers. Alternatively, genes can be isolated by screening a genomic library, using probes. At least one 3' untranslated region should be isolated from the host or closely related organism, preferably from a highly expressed gene.

The SSU coding sequence has regions that are highly conserved among different organisms (Goldschmidt-Clermont et al. (1986) J. Mol. Biol. 191:421–432; Yamamoto et al. (1988) Nucl. Acides Res. 16:11830; Greenland et al. (1987) Planta 170: 99–110; Coruzzi et al. (1984) EMBO J. 3:1671–1679; Wolter et al. (1988) pNAS USA 85:846–850; and Piinck et al. (1984) Biochemie 66:539–545). These regions are long enough to make probes for either PCR amplification or library screening. At the amino acid level, one such conserved region is amino acids 124 to 141 (Chlamydomonas numbering). In the absence of codon bias information, potential probe sequences based on this region are some subset of:

TAiTAiGAiGGiiGiTAiTGGACiATGTGGAAiiTiCCiATGTTiGG or its complement, where i represents points of ambiguity in the backtranslation of the amino acid sequence, and the capital letters are DNA bases.

A glycolysis gene for which considerable sequence data is available is pyruvate kinase. Enzymes of glycolysis are usually well expressed in anaerobic conditions. Verification of enzyme activity in anaerobic conditions is done using well known biochemical methods (Burke et al. (1983) J. Biol. Chem. 258:2193-2201). Alternatively, expression at the RNA levels is measured by, for example, using probes synthesized using known sequences or Northern blots, RNA-ase protection, or primer extension, Sambrook, J. et al. (1989) supra.

Pyruvate kinase has sequence domains that are highly conserved between different organisms (O'Hara et al. (1989) PNAS USA: 86:6883-6887; Lonberg et al. (1983) PNAS USA 80:3661-3665; Burke et al. (1983) J. Biol. Chem. 258:2193-2201; and Tani et al. (1988) PNAS USA 85:1792-1795). At the amino acid level two conserved domains are (single letter amino acid code) LDTKGPEIRT and MVARGDLG corresponding to amino acids 65 to 74 and 241 to 248 of the $E.$ $coli$ protein. These regions are long enough to make probes for either PCR amplification or library screening. In the absence of codon bias information, potential probe sequences are: TiGAiACiAAiGGiCCiGAiAT (or its complement) and CiATGGTiGCiiGiGGiGA (or its complement), where i indicates points of ambiguity in the back translation of the amino acid sequence.

Amplification of genes using PCR is well known, and can be done following the methods of (Innis et al. (1990) supra), for example. The object of the PCR amplification is the isolation of the sequences flanking the coding sequences. Since only the coding sequences are known, a method such as inverse PCR (IPCR) or anchored PCR is preferably used. The products of the amplification are cloned and some of the clones are sequenced. The translation start and stop sites are determined from the gene structure (Wasylyk, B. (1986) Protein Coding Genes of Higher Eukaryotes: Promoter Elements and Trans-acting Factors. In: Maximizing Gene Expression, Reznifoff, W. and Gold, L. eds., Butterworths, Boston), or from standard laboratory techniques (Sambrook et al. (1989) supra).

Library construction and screening are carried out using established methods (Sambrook et al. (1989) supra), with no special alterations in technique for application to algae. The object of such experiments is the isolation of a clone of a gene for, e.g., SSU or pyruvate kinase using probes based on conserved sequences. Alternatively, the object of such experiments is to isolate a gene that is highly expressed, or a gene that is highly expressed under anaerobic conditions. Again, such techniques are well established and are generally applicable (Sambrook et al. (1989) supra).

Promoter constructs are tested first by electroporation of algal protoplasts or other transient expression system, e.g., ballistic DNA delivery. The promoter of interest is placed in front of a reporter gene that is readily assayed, such as GUS, LUC, or ADH and the 3' region is placed after the reporter gene. The DNA is introduced into the host tissue, the cells are cultured for a period to permit gene expression, e.g., two days, and the cells are assayed for reporter activity. Promoter constructs are subsequently used for stable transformation, and their activity is assessed to determine promoter activity in stable transformants.

4. Choice of Selection and Screening Coding Regions

Potential selectable markers include resistances to kanamycin, hygromycin, spectinomycin, streptomycin, sulfonyl urea and other drugs for which corresponding resistance genes have been isolated. Algae can in general be cultured photoautotrophicly, so drugs affecting chloroplast function can be lethal.

Potential markers are evaluated by determining sensitivity of the potential host plant to the drug. If the potential host plant is sensitive to a concentration range of the drug similar to that found in a higher plant successfully transformed with the corresponding resistance marker and isolated on the basis of its drug resistance, then the drug and its resistance gene are judged to be appropriate.

5. Transformation Constructs

Constructs used in transformation include a construct with at least one of PDC and ADH, driven by an appropriate promoter, and with an appropriate 3' untranslated region. The construct may contain coding and associated non-coding sequences for both PDC and ADH, and may contain in addition, coding and associated non-coding regions for one or more selectable or screenable markers. The 5' and 3' non-coding regions may be the same for all genes, or they may be different. If the construct contains only one of PDC or ADH, then it may be necessary to make an additional similar construct but for the gene not already incorporated. Additional constructs may be useful for testing transformation methods, or the efficacy of selectable or screenable markers.

Examples of such transformation constructs are as follows:

1. LUC
2. ADH
3. PDC
4. KAN$^r$ with ADH
5. KAN$^r$ with LUC and ADH
6. HYG$^r$ with PDC
7. HYG$^r$ with GUS and PDC
8. KAN$^r$ with ADH and PDC

D. TRANSFORMATION

1. DNA Delivery Method

DNA delivery techniques include electroporation, PEG induced uptake, and ballistic delivery of DNA (Potrykus (1991) supra); Agrobacterium is a less preferred route. The first two techniques involve the use of protoplasts. Production of protoplasts followed by regeneration is known for several species of algae, including *Enteromorpha linza, Enteromorpha intestinalis, Ulva pertusa, Ulva taeniata, Monostroma zostericola* in the Chlorophyta, as well as members of Genera Laminaria, Undaria, Macrocystis, Sargassum and Dictyosiphon in the Phaeophyta and Porphyra, Chondrus, Gelidium and Agardhiella in the Rhodophyta (Cheney (1986) In: Algal Biomass Technologies, Barclay et al. (eds.) J. Cramer, Berlin). For Enteromorpha, DNA delivery by electroporation or PEG induced uptake are the most attractive methods, since protoplast preparation and regeneration are both feasible (Saga et al. (1986) ibid., Polne-Fuller et al. (1986) ibid., Reddy, C. R. K. et al. (1989) Botanica Marina 32:483–490; Polne-Fuller et al. (1987), Tissue culture of seaweeds. In: *Seaweed Cultivation for Renewable Resources*, Bird and Benson (eds.), Elsevier, Amsterdam). The exact conditions for DNA uptake are dependent on the species and isolate used.

DNA delivery by electroporation is optimized by using a construct with a 5' region that gives at least some activity and is fused to a reporter gene the expression of which can be measured with great sensitivity, such as the LUC gene. For example, protoplasts prepared as described in Saga et al. (1986) supra) are suspended to a concentration of about $10^5$ to $10^6$ protoplasts/ml in a medium containing 1.2M sorbitol, 3.5 mM $CaCl_2$ and 0.1M Tris buffer pH 8.0, and in addition, 100 micrograms/ml of plasmid DNA bearing the LUC gene, such as transformation construct 1(LUC) listed in part C(5) above. An electrical voltage is applied to a ½ ml sample which is than diluted into 10 ml of m-PESI medium (Provasli (1968) In: *Culture and Collection of Algae*, Watenabe et al. (eds.) Japan Soc. of Plant Phys. pp. 63–75) and cultured for 2 days at 24° C., 12/12 L/D, 50–100 microeinsteins/m²/sec. After two days, LUC is assayed by standard methods (Ow et al. (1986) Science 234:856–859). By treating different samples with different electrical conditions, i.e., with different combinations of voltage and pulse length, the optimal conditions for electroporation are determined (the combination of conditions that gives the highest LUC activity). Electrical conditions tested are in the range of 200 to 2000 V/cm, with duration from 10 microseconds to 500 milliseconds. Electrical conditions that are too harsh will result in the death of the cells, while conditions that are too gentle will fail to render the cell membrane permeable to DNA.

Other DNA delivery methods are also available. Instead of electroporation, treatment with a range of PEG concentrations is tested in a similar fashion, assaying reporter (e.g., LUC) activity after two days. Treatment with Agrobacterium, followed by assay for reporter (e.g., LUC) is also possible; this requires in addition that the transformation constructs be in an appropriate vector, and that the assays be carried out after Agrobacterium has been killed. Agrobacterium can be eliminated by use of antibiotics such as carbenicillin, and by washing the cells with media which do not contain a carbon source, such as m-PESI. Elimination of Agrobacterium is necessary because of the possibility that the algal promoter will have some activity in the bacterium, which would result in false positive results to the transformation experiment.

2. Choice of Tissue for Transformation

An alga with simple thallus structure is preferred. In Enteromorpha, a preferred system, the vegetative thallus is composed of primarily a single cell type and a single tissue type, and a small proportion of the cells form rhizoids. The entire plant can be used without need for separation of cell types.

3. Isolation of Transformants

Protoplasts or explants subjected to a transformation protocol are grown in the presence of antibiotics to which the marker genes confer resistance. Alternatively, plants can be screened for the presence of a reporter such as LUC. Zoospore production followed by selection or screening can be used to resolve chimeras.

E. ETHANOL PRODUCTION

1. Geographical Region

Algae can be grown essentially anywhere on the surface of the earth. Economic considerations give preference to regions that have a plentiful supply of light and water, year round moderate temperature and in which the creation of large flat ponds is relatively inexpensive. There is some preference for regions not suitable to other forms of agriculture, e.g., deserts for which only seawater irrigation is available. If sea water is used as the water source, proximity to same is desirable to minimize pumping costs. Elevation is preferably less than 1000 m above the elevation of the water source, and most preferably less than 200 hundred meters above the elevation of the water source.

2. Pond Characteristics

Ponds for algal growth should be level and have a shape that is convenient for covering, in order to generate the anaerobic condition. If a cover is moved from pond to pond, adjacent ponds should have the same size and shape. Economic considerations give preference to large ponds, but size is limited by the time required to completely drain the pond. Drain time depends on the resistance to flow of the perticular alga used. Maximum pond length (i.e., the dimension parallel to the flow of water) is expected to be on the order of a few hundred meters or less.

The bottom and sides of the pond must have a limited rate of leakage to prevent excess water usage or excess loss of fermentation medium. This can be achieved by methods used for construction of water reservoirs, such as plastic liners or clay seals if the leakage rate of the unmodified soil is too high. Daily evaporation depends on weather conditions, but it is about 1 cm per day. Leakage rates are preferably less than the evaporation rate, e.g., less than 1 cm per day, and most preferably less than 0.2 cm per day with a 4 cm head. During fermentation, leakage will result in the loss of product. If fermentation occurs in a 4 day period with a fermentation volume 2 cm deep, with a total head of 4 cm, then leakage should be less than 0.5 cm per day with a 4 cm head. Leakage rates are preferably less than 0.2 cm per day with a 4 cm head, most preferably less than 0.05 cm per day with a 4 cm head. If fermentation occurs in a shorter period, e.g., 1 day, then acceptable leakage rates are correspondingly larger, e.g., 0.2 cm per day.

3. Water Supply

Water supply must be sufficient to replace water lost to evaporation. If saline water is used, it is additionally necessary to drain off water that is too salty and replace it, so that total water consumption is greater than the total evaporation rate, to an extent depending on the tolerance to salinity of the algae.

4. Fermentation

For ethanolic fermentation, it may be desirable to make the algal culture anaerobic. This can be accomplished by covering the field with an oxygen impermeable material such as polyethylene. Respiration will utilize the oxygen dissolved in the covered water. The anaerobic algae will then ferment. Ethanol produced during fermentation will be distributed between the algal mass and the surrounding growth medium. When the pond is drained and washed, this ethanol is removed with the growth medium. The alcohol can be removed from the harvested growth medium, or the growth medium can be used on another pond for fermentation, resulting in an increase in alcohol concentration. The optimum alcohol concentration depends on the economics of alcohol separation, the alcohol tolerance of the organism, and the economics of reusing fermentation medium.

The pond cover should restrict the movement of oxygen to such a degree that the culture becomes anaerobic. Tolerable rates of oxygen leakage depend on the rate of respiration of the algal mat. For example, if respiration occurs at a rate of 0.4 moles $O_2$ per $m^2$ in 24 hour, then oxygen diffusion through the cover at a rate of 277 micromoles/min-$m^2$ would be sufficient to support aerobic respiration. Oxygen diffusion should be less than the rate required to support aerobic respiration, preferably less than 10% of the rate required to support aerobic respiration, and most preferably less than 1% of the rate required to support aerobic respiration. If the edges of the cover are not sealed, oxygen may diffuse in from the edges through the water medium. Acceptable leakage at the cover edges depends on respiration rate and pond geometry. The part of the algal mat close enough to the edges to respire aerobicly is not productive. This non-productive fraction is preferably less than 10% of the total pond area, most preferably less than 1%.

The pond cover is preferably removable to permit photosynthesis in between periods of fermentation. For example, a sheet of polyethylene is moved from a pond done fermenting to an adjacent pond, which then begins its fermentation period. The cover should also be capable of withstanding ordinary stresses encountered in the field, such as UV light exposure and wind. For example, a sheet of polyethylene containing carbon black pigmentation and reinforced with, for example, nylon cord is a suitable cover.

5. Physiological Parameters and Productivity

Production is limited by the net rate of carbon fixation, hence it depends on photosynthesis and respiration. In addition, productivity is reduced by the amount of time required for fermentation, so productivity also depends on fermentation rate. The maximum increase in alcohol concentration that can be achieved in one pass of fermentation depends on the amount of starch stored per unit volume.

6. Purification of Ethanol

Ethanol is purified from the fermentation medium by distillation, membrane purification, chemical drying, or some combination of these, using known techniques. Ethanol is produced either as 95% ethanol or dried to 100%, depending on the intended end use.

The following example is offered by way of illustration, not by way of limitation.

EXPERIMENTAL

Example 1

Inocula from the field collected in the spring were grown in full sun, in still shallow water, with local water from San Francisco bay supplemented with sodium nitrate (0.2 g/l) and sodium phosphate (0.1 g/l). Water was replaced when salinity reached 1.5 osmolal. Within several weeks a rapidly growing Enteromorpha sp. was evident in these cultures. Within two months it had formed a dense mat in the growth pond, excluding all other algae. A similar isolation carried out in the fall gave a similar result.

Photosynthetic rate, respiratory rate, uncoupled respiratory rate, growth density and starch content were determined for the Enteromorpha species isolated as described above. Photosynthetic rate was determined using an oxygen electrode (Yellow Springs Instrument Co.) and a specially constructed chamber. The chamber held a 6 cm diameter sample of algal mat, 200 ml of seawater and 50 ml of air. The chamber was provided with an aluminum heat exchanger which was immersed in a water bath at 30° C. The oxygen electrode operated in the gas phase. Output of the oxygen electrode was recorded with a Bascom-Turner chart recorder. The large gas phase volume of this chamber makes it too insensitive for convenient measurement of respiration, but suitable for photosynthetic measurement. The sample of algal mat was partially submerged. The sample chamber with sample was equilibrated with the atmosphere for one hour with illumination of 1500 microeinsteins/$m^2$ sec PAR before measurements were initiated. No $CO_2$ supplementation was used. Results are shown in Table 1.

TABLE 1

| | Photysynthetic Rate vs. Light Intensity | |
|---|---|---|
| Sample | light intensity u-einsteins/$m^2$-sec | g carbohydrate/$m^2$-hr |
| 1 | 0 | −0.25 |
| 2 | 0 | −0.51 |
| 3 | 216 | 0.93 |
| 4 | 442 | 3.60 |
| 5 | 637 | 4.56 |
| 6 | 884 | 5.17 |
| 7 | 1017 | 8.27 |
| 8 | 1238 | 8.78 |

Photosynthetic rate in this organism is as expected for a plant adapted to full sunlight, and corresponds to a daily rate of about 70 g/$m^2$.

Respiratory rate was measured on samples of algal mat in a 1.5 ml unstirred water volume, using the YSI oxygen electrode, calibrated in unstirred water. Samples were dark adapted for one hour before measurment. Dim light can stimulate respiration about 3 fold, see Table 2.

TABLE 2

| Stimulation of Respiration by Dim Light in Dark Adapted Enteromorpha | |
|---|---|
| Time in light (hrs.) | Respiration Relative to Control |
| 0 | 1 |
| ¼ | 1.95 |
| ½ | 2.90 |
| 1 | 3.75 |
| 1¼ | 3.52 |

Dark respiratory rate corresponds to a nightly rate of 7 g/$m^2$ for a mat with 10 kg fresh weight /$m^2$. In order to obtain a lower bound on the maximum potential rate of glycolytic enzymes (and other respiratory steps), the respiratory rate was also determined after treatment with 1 mM DNP for 1 hours. The uncoupled rate is about 10 fold greater than the dark rate, indicating substantial capacity to increase the rate of glycolysis during anaerobiosis. Respiratory data are summarized in Table 3.

TABLE 3

| Sample | Respiration Rate umoles O$_2$/g-hr |
| --- | --- |
| 1 | 1.20 |
| 2 | 3.18 |
| 3 | 5.42 |
| 4 | 3.95 |
| 5 | 2.80 |
| 6 | 1.54 |
| 7 | 1.87 |
| 8 | 4.16 |
| 9 | 2.38 |
| 10 | 4.88 |
| Average for 1-10 | 3.14 |
| Stand. Dev. for 1-10 | 1.43 |
| 11 | 10.9 |
| 12 | 48.7 |
| 13 | 59.2 |
| Average for 11-13 | 39.6 |
| Stand. Dev. for 11-13 | 25.4 |

Note: Items 11-13 above are with 1 mM DNP.

Starch content was determined for several samples using the sulfuric acid-phenol method. Samples were blotted, weighed and then incubated in 40% sulfuric acid for one hour. This treatment dissolves the starch but leaves cell walls largely intact. A sample of the 40% sulfuric acid was tested for reducing sugars using phenol/sulfuric acid and absorption at 485 nm. The reducing sugar test was calibrated with glucose standards. Starch content is summarized in Table 4.

TABLE 4

| Experiment # | Growth Conditions | Starch Content ug Starch/mg Fresh Weight Reducing Sugars | Standard Deviation |
| --- | --- | --- | --- |
| 1 | Shade | 42.5 | 2.45 |
| 2 | Bright Light | 78 | 13 |
| 3 | Bright Light | 80.2 | 12.2 |

The apparent starch content is about 80 mg/gram fresh weight, and of this at least 40 mg/g is readily respired.

Fresh weight was determined for mat samples of known dimensions. For both 2 cm and 1 cm thick mats, the growth density was 0.5 g fresh weight/cc.

The values for physiological parameters from Enteromorpha can be used to demonstrate the potential for alcohol production by this method. With a standing biomass of 10,000 grams fresh weight per square meter, photosynthesis of 70 g/m$^2$-day, respiration of 7 g/m$^2$-night, expected starch accumulation is about 63 g/da/m$^2$ to 378 grams/m$^2$ (about 6 days of photosynthesis). The resulting fermentation would increase the alcohol concentration of 20 liters/m$^2$ of fermentation medium (i.e. 2 cm deep) by about 1.25%. Assuming a 20% extra wash volume, 4 passes of this medium would give 4% ethanol, which would be distilled or otherwise separated from the medium. The fermentation step would occur under an opaque cover (e.g. black polyethylene) to exclude oxygen and light. In order for the process to be efficient, the fermentation should proceed rapidly and produce mainly alcohol. The rate of fermentation is naturally higher with a larger standing biomass. Because this also increases the respiration rate, the rate of fermentation should be high relative to the rate of respiration (e.g., at least one to five times as high). The observed increase in respiratory rate with DNP gives a lower bound on the capacity of the system to increase glycolytic rates. A six fold increase in the rate of substrate utilization during fermentation gives a fermentation rate of 42 g/m$^2$-12 hours, so about 4½ days of fermentation would be required to harvest 6 days of photosynthesis. The efficiency of the method would be about 57% of the theoretical maximum, with fermentation rate the major limiting factor. The theoretical maximum rate for this alga is 63 g/m$^2$×365 da/yr×1 kg/1000 g×10,000 m$^2$/ha or about 230 metric tons per hectare per year, so the expected yields are over 100 metric tons per hectare per year for this alga. Yields depend on starch replacement rates, not on growth rate of biomass or storage organs such as seeds or tubers. There are constraints in addition to the rate of carbon fixation on the growth of biomass and storage organs. For this reason, the inherent productivity of a field fermentation is higher than can be achieved with traditional agriculture.

The rate of alcohol production in the unengineered organism was measured, using a kit designed for the detection of alcohol (Lunddquist (1957) In: Methods in Biochemical Analysis, Vol. VII, Glick (ed.), Interscience, New York, pp. 217-251). The average rate for 4 samples was 12 ul ethanol/g-hr (freshweight basis). This rate is sufficient to increase the alcohol content of the growth medium by about 0.065% in 4½ days.

PROTOPLAST PREPARATION

Axenic algal cultures, Polne-Fuller, M. (1987), supra, are transferred to protoplasting medium consisting of 1.2M sorbitol, 3.5 mM CaCl$_2$, 0.1M Tris buffer pH 8.0 and 2% Onazuka cellulase r10 (Saga et al. (1986) supra). After several hours, the protoplasts are separated from the cell wall debri by filtration, using a sterile 60 micron nylon mesh. Protoplasts are washed 3 times in sterile wash medium, (same as protoplasting medium but without enzymes) (Saga et al. (1986) supra).

PROTOPLAST CULTURE

Protoplasts may be used for transformation experiments described below, and cultured by dilution into liquid in PESI medium, and subsequently grown in sterile seawater supplemented with sodium nitrate, sodium phosphate, micronutrients and vitamins. Appropriate mixes for algal culture are commercially available, e.g., from Sigma.

The sensitivity to antibiotics is determined for protoplast derived cultures. Various concentrations of kanamycin ranging from 25 to 500 mg/l are tested for efficacy in killing protoplast derived colonies of cells from 2 days to 3 weeks after protoplasting. In this way the minimum concentration that gives reliable killing is determined.

DNA ISOLATION

Isolation of DNA from algae is carried out by first making protoplasts as described above. This minimizes contamination by algal polysaccharides. Cells are lysed by suspending in distilled water, and DNA isolated as described in, for example, Sambrook et al. (1989) supra. DNA is isolated from about 50 mg of protoplasts.

PCR PROBE DESIGN

Divergent PCR amplification probes are synthesized using a conserved region of the small subunit of ribulose bisphophate carboxylase. One probe (SSU 3') is 22 bp long and has the sequence 5'-TiCCiATGTTiGGiT-GiACiGA-3'. This sequence corresponds to the back-translation of the most conserved region of the RBCS amino acid sequence in a comparison of potato, pine, and Chlamydomonas, and is intended to extend toward the 3' untranslated region of the gene. Inosine (i) is used at positions where there is ambiguity due to the degeneracy of the genetic code. Another probe (SSU 5') of 23 bp is synthesized that has the sequence 5'-TTCCACATiGTCCAiTAiCiiCC3'. This sequence is complementary to an adjacent region of the consensus sequence, and is intended to extend toward the promoter region.

IPCR of SSU

The IPCR procedure (Innis et al. (1990), PCR protocols. Academic Press, New York) is used to amplify the regions of the genome containing sequences homologous to the RBCS gene, using restricted nuclear DNA and using polymerase with proofreading function (New England Biolabs, DNA Polymerase Technical Bulletin, (1991), New England Biolabs, Beverly, Mass.) to ensure long, error-free transcripts. The PCR product is cleaved enzymaticly between the 5' and 3' flanking regions, and these are cloned, using PCR cloning techniques, into pUC19 digested with SphI and SacI (Holton et al. (1991) Nucl. Acids Res. 19:1156). Thirty six colonies are examined for insert size and those with the largest inserts are chosen. These are tested for the presence of regions with homology to the original probes by PCR amplification using the probes described above and pUC19 (Yanisch-Perrou et al. (1985) Gene 33:103-119) sequencing probes, one of which primes on the HindIII side of the polylinker (pUC HindIII), and the other of which primes on the EcoRI side of the polylinker (pUC EcoRI) to the opposite DNA strand. Amplification is carried out with the primer pairs SSU 3' and pUC EcoRI; SSU 5' and pUC HindIII. Clones that are PCR positive will have the 5' end of the gene fragment toward the HindIII site and the 3' end of the gene fragment toward the EcoRI site of the pUC19 polylinker. Five clones are chosen with 5' flanking region inserts (pESSU5 1-5) and five with 3' flanking region inserts (pESSU3 1-5).

Plasmids pESSU5 1-5 and pESSU3 1-5 are sequenced, using standard sequencing methods (Sambrook et al. (1989) supra) and primers designed for pUC19. Translation initiation and termination sites are identified, based on recognition of such features as TATA box, open reading frame and initiation codon at the 5'end, and open reading frame, possible polyadenylation site and termination codon at the 3' end. Sequencing determines unambiguously whether clones are redundant.

PCR is used to introduce a new restriction site at the 3' end of the 5' flanking fragments, and eliminate the coding sequences. The new site is an NcoI site which includes the ATG translation initiation codon. The PCR product is cloned into pUC 19 restricted with HindIII. Similarly, PCR is used to introduce a new restriction site at the 5' end of the 3' flanking fragments, and eliminate the coding sequences. The new site is an XbaI site which includes the translation termination codon TAG. The PCR product is cloned into pUC 19 restricted with SmaI. From 200 to 1000 bp 5' to translation start are retained in three clones, pEU5 1-3. From 200 to 500 bp 3' to the translation stop are retained in three clones, pEU3 1-3.

Plasmids pEU5 1-3 and pEU3 1-3 are digested with XbaI and KpnI restriction enzymes. This results in linearization and release of a very short DNA fragment from the pEU5 plasmids, and release of the 3' untranslated fragment from the pEU3 plasmids. Plasmids pEU5 1-3 are combined in a pair-wise fashion with fragments from pEU3 1-3, to give plasmids pEU 1-9. All of these plasmid have a 5' untranslated region bounded on the 3' end by a unique NcoI site and a 3' untranslated region bounded on its 5' end by an XbaI site.

The LUC coding region is cut from DNAP plasmid pJJ3792 which contains the LUC coding region bounded by an NcoI site at the 5' end and an XbaI site at the 3' end. Alternatively, plasmid pD0432 (Ow et al. (1986) Science 234:846-859) could be used. This plasmid lacks the NcoI site at the ATG. Such a site could be introduced, or a gene fusion could be constructed without such a site by known methods (Sambrook et al. (1989) supra). The cut is done using restriction enzymes NcoI and XbaI. Plasmid pEUI is also cut with NcoI and XbaI, and the products of these reactions are mixed and ligated and used to transform E. coli. Colonies are screened by making DNA minipreps to detect plasmid with an appropriate insert, i.e., a plasmid that, when cut with NcoI and XbaI gives two fragments, one the size of the plasmid plus untranslated regions and the other the size of the LUC coding region. This procedure is repeated for each of pEU2 through 9.

The LUC constructs thus produced, pEULUC 1-9 are tested for activity in a protoplast transient activity assay. Protoplasts are prepared as described above from axenic Enteromorpha cultures. A large scale plasmid prep is made from each of the LUC constructs developed as described above. For electroporation, protoplasts are suspended in a medium similar to that used for protoplasting (Saga et al. (1986) supra). The principal osmoticum is sorbitol 1.2M, with $CaCl_2$, 3.5 mM and Tris buffer, pH 8.0, 20mM, as well as DNA, 100 micrograms per ml. Conductivity is adjusted with NaCl. Electrical conditions are chosen such that a field strength in the range of 100 to 1000 V/cm is applied for a duration in the range of 1 ms to 100 ms. After electroporation, the cells are cultured and transferred to culture medium, described above. After two days of culture, the cells are assayed for LUC activity (Ow et al. (1986) supra). The different LUC plasmids are compared for transient activity at optimal electroporation conditions. The plasmid whose derivative gives the greatest activity is used for further constructions.

For stable transformation, the coding sequence for NPTII is cut from DNAP plasmid pJJ187 which contains the NPTII coding region bounded by an NcoI site at the 5' end and an XbaI site at the 3' end. Alternatively, plasmid pUB110, an NPT-II containing plasmid available from Sigma (Gryczan et al. (1978) J. Bacteriology 134:318) could be used. This plasmid lacks the NcoI and XbaI sites. Such sites could be introduced or a gene fusion could be constructed without such sites by known methods (Sambrook et al. (1989) supra). The cut is done using NcoI and XbaI. The plasmid bearing the untranslated region is cut with NcoI and XbaI, and the products of this reaction are mixed and ligated to give plasmid pEUKAN.

Protoplasts made as described above are transformed using electroporation conditions as described above, except that the DNA consists of a mixture of plasmids pEULUC and pEUKAN. Treated protoplasts are cultured in selective media, and surviving colonies are screened for LUC activity when they reach a size of about 100 cells. Approximately 10% of the transformants are LUC positive. Twelve of these are tested to confirm the presence of the NPTII gene using PCR.

The coding sequence for ADH bounded by NcoI and XbaI sites is cloned from a yeast RNA prep using reverse transcriptase followed by PCR amplification using the primers 5'-ACCATGGCTATCCCAGAAACTCAA-3' and 5'-GTCTAGATAGAAGTGTCAACAACGTATC-3'. Reverse transcriptase is available from commercial sources. e.g., Sigma. Yeast RNA can be prepared from Saccharomyces cerevesiae by known methods (Innes et al. (1990) PCR protocols. Academic Press, New York; Sambrook et al. (1989) supra). The product of the PCR amplification is cloned into pUC19, to make plasmid pADH.

The coding sequence for PDC bounded by NcoI and XbaI sites is cloned from a yeast RNA prep using reverse transcriptase followed by PCR amplification using the primers 5'-TCCATGGCTGAAATTACTTTGGGT-3' and 5'-GTCTAGACAAGTTTTGTGGAGCAATC-3'. The product of the PCR amplification is cloned into pUC19, to make plasmid pPDC.

Plasmid pADH is cut with NcoI and XbaI, and plasmid pEU1 is cut with NcoI and XbaI, and the products of these reactions are mixed and ligated, used to transform $E.\ coli$ and resultant clones screened for the presence of appropriate restriction fragments. This results in development of the plasmid pEUADH, which has the ADH coding sequence flanked by the Enteromorpha untranslated regions.

Plasmid pPDC is cut with NcoI and XbaI, and plasmid pEUI is cut with NcoI and XbaI, and the products of these reactions are mixed and ligated, used to transform $E.\ coli$ and resultant clones screened for the presence of appropriate restriction fragments. This results in development of the plasmid pEUPDC which has the PDC coding sequence flanked by the Enteromorpha untranslated regions.

Over $10^7$ protoplasts are transformed as described above, except that the DNA is a mixture of pEUKAN, pEUADH and pEUPDC. The protoplasts are cultured in a selective medium containing kanamycin. One thousand of the surviving transformants are screened for alcohol production under anaerobic conditions, using a mixture including 100 U/ml ADH, 2mM NAD+ and Schiff reagent, prepared by treating 5 mg pararosaniline with 25 mg sodium bisulfite in 100 ml of medium. Plants showing readily detectable alcohol production under anaerobic conditions are retained for further study.

Alcohol-producing transformants (e.g., up to ten) are subcultured and grown up in the greenhouse on tiles in uncovered magenta boxes in 200 ml of seawater medium. When the cultures have reached a density of 0.5 g fresh weight per $m^2$, they are tested for respiration rate, photosynthetic rate, starch content and fermentation rate. Respiration and photosynthesis are measured using the oxygen electrode and a chamber in which the tiles to which the cultures are attached fit. The chamber should be air tight and transparent on top. Starch content is measured using the $H_2SO_4$/phenol method for detection of reducing sugars. Fermentation rate is determined by measurement of alcohol production. Alcohol production rate is determined both in anaerobic and aerobic conditions.

The isolates (e.g., two) that show the best combination of physiological traits are grown up further and used to demonstrate alcohol production on a small scale. Cultures are established in shallow ponds in the greenhouse. The ponds have concrete bottoms and sides. They are provided with water inlet and drain fittings. Total area is approximately ¼ $m^2$. Cultures are flooded with seawater every 2 to 3 days to a depth of 3 cm. After 2 to 3 days the remaining water is drained off and the cultures are permitted to air dry for 1 to 3 hours. Cultures are then reflooded. Every ten to fifteen days the cultures are flooded and covered with an opaque black sheet of polyethylene to exclude oxygen and light. The edges of the sheet are held in place by weights, and the top of the sheet is flooded with water to a depth of approximately 2 cm. The medium is drained off from under the sheet until the sheet presses down on the algal mat. The mat is allowed to ferment for approximately 24 hours. The fermentation medium is drained off and the mat is rinsed with seawater, with the cover still in place. The volume and alcohol content of the fermentation medium is determined. In small scale studies such as this, ethanol may be measured by assay, e.g., using the ADH/NAD spectrophotometric method detailed earlier. Isolates capable of producing over 50 grams of alcohol per $m^2$ in 24 hours are retained.

The retained isolates are grown up using known methods (Bird (1987) supra), to a mass on the order of 10×greater, and then used for seeding a pond of a size on the order of one hectare surface area. The process is then carried out in the pond in the same way as described above for the process under greenhouse conditions, but with appropriate scale up. Ethanol is isolated via distillation using known techniques.

Although the foregoing invention has been described in detail for purposes of clarity of understanding, it will be obvious that certain modifications may be practiced within the scope of the appended claims.

All references cited herein are incorporated by reference.

---

What is claimed is:

1. A method for producing a metabolic product in algae, said method comprising:
   growing in a growth medium algal cells of the genus Enteromorpha which overexpress at least one enzyme in a metabolic pathway for the product, wherein the product is soluble and secreted into the growth medium and wherein cell protoplasts have been transformed with a recombinant DNA construct carrying a gene encoding said one enzyme under the control of a heterologous high expression level promoter selected from the group consisting of a SSU promoter and a pyruvate kinase gene promoter; and recovering the metabolic product from the growth medium.

2. A method as in claim 1, wherein the algal cells express multiple copies of the gene expressing the one enzyme.

3. A method as in claim 1, wherein the metabolic product is ethanol and the enzyme is PDC or ADH.

4. A method as in claim 3, wherein the algal cells overexpress both PDC and ADH.

5. A DNA construct comprising:
a DNA sequence encoding an enzyme in a metabolic pathway of algae of the genus Enteromorpha, wherein the metabolic pathway produces a soluble metabolic product; and
a heterologous promoter sequence connected to a 5'-end of the DNA sequence, wherein said promoter will provide a high level of expression of the enzyme under at least some algal growth conditions and is selected from the group consisting of a SSU promoter and a pyruvate kinase promoter.

6. A DNA construct as in claim 5, wherein the metabolic product is ethanol and the enzyme is PDC or ADH.

7. A DNA construct as in claim 5, further comprising a marker gene.

8. Algal cells of the genus Enteromorpha capable of overexpressing at least one enzyme in a metabolic pathway for a soluble metabolic product, wherein cell protoplasts have been transformed with a recombinant DNA construct carrying a gene encoding said one enzyme under the control of a heterologous high expression level promoter selected from the group consisting of a SSU promoter and a pyruvate kinase promoter.

9. Algal cells as in claim 8, wherein the gene for the one enzyme is a yeast gene.

10. Algal cells as in claim 8, wherein the cells express multiple copies of a gene expressing the one enzyme.

11. Algal cells as in claim 8, wherein the metabolic product is ethanol and the enzyme is PDC or ADH.

12. Algal cells as in claim 11, wherein the algal cells express a gene for PDC or ADH under the control of an algal promoter other than the PDC or ADH promoter.

13. Algal cells as in claim 11, wherein the algal cells overexpress both PDC and ADH.

14. Algal cells as in claim 11, wherein the enzyme and the promoter are encoded on a DNA sequence which has been integrated into the genome.

15. Algal cells as in claim 14, wherein the PDC or ADH gene are encoded on the DNA sequence under the control of the SSU promoter or the pyruvate kinase promoter.

16. Algal cells transformed with the DNA construct of claim 5.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:1:

TANTANGANG GNNGNTANTG GACNATGTGG AANNTNCCNA TGTTNGG    47

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Leu Asp Thr Lys Gly Pro Glu Ile Arg Thr
1           5                   10

( 2 ) INFORMATION FOR SEQ ID NO:3:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

Met Val Ala Arg Gly Asp Leu Gly
1               5

( 2 ) INFORMATION FOR SEQ ID NO:4:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:4:

TNGANACNAA NGGNCCNGAN AT    22

( 2 ) INFORMATION FOR SEQ ID NO:5:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:5:

CNATGGTNGC NNGNGGNGA    19

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:6:

TNCCNATGTT NGGNTGNACN GA    22

( 2 ) INFORMATION FOR SEQ ID NO:7:

( i ) SEQUENCE CHARACTERISTICS:
       ( A ) LENGTH: 23 base pairs
       ( B ) TYPE: nucleic acid
       ( C ) STRANDEDNESS: single
       ( D ) TOPOLOGY: linear ( i i ) MOLECULE TYPE: DNA (probe)

( x i ) SEQUENCE DESCRIPTION: SEQ ID NO:7:

TTCCACATNG TCCANTANCN NCC                                           2 3

( 2 ) INFORMATION FOR SEQ ID NO:8:

( i ) SEQUENCE CHARACTERISTICS:
       ( A ) LENGTH: 24 base pairs
       ( B ) TYPE: nucleic acid
       ( C ) STRANDEDNESS: single
       ( D ) TOPOLOGY: linear ( i i ) MOLECULE TYPE: Primer ( x i ) SEQUENCE DESCRIPTION: SEQ ID NO:8:

ACCATGGCTA TCCCAGAAAC TCAA                                          2 4

( 2 ) INFORMATION FOR SEQ ID NO:9:

( i ) SEQUENCE CHARACTERISTICS:
       ( A ) LENGTH: 28 base pairs
       ( B ) TYPE: nucleic acid
       ( C ) STRANDEDNESS: single
       ( D ) TOPOLOGY: linear ( i i ) MOLECULE TYPE: Primer ( x i ) SEQUENCE DESCRIPTION: SEQ ID NO:9:

GTCTAGATAG AAGTGTCAAC AACGTATC                                      2 8

( 2 ) INFORMATION FOR SEQ ID NO:10:

( i ) SEQUENCE CHARACTERISTICS:
       ( A ) LENGTH: 24 base pairs
       ( B ) TYPE: nucleic acid
       ( C ) STRANDEDNESS: single
       ( D ) TOPOLOGY: linear ( i i ) MOLECULE TYPE: Primer ( x i ) SEQUENCE DESCRIPTION: SEQ ID NO:10:

TCCATGGCTG AAATTACTTT GGGT                                          2 4

( 2 ) INFORMATION FOR SEQ ID NO:11:

( i ) SEQUENCE CHARACTERISTICS:
       ( A ) LENGTH: 26 base pairs
       ( B ) TYPE: nucleic acid
       ( C ) STRANDEDNESS: single
       ( D ) TOPOLOGY: linear ( i i ) MOLECULE TYPE: Primer ( x i ) SEQUENCE DESCRIPTION: SEQ ID NO:11:

GTCTAGACAA GTTTTGTGGA GCAATC                                        2 6